United States Patent
Nedu et al.

(10) Patent No.: US 8,128,870 B2
(45) Date of Patent: Mar. 6, 2012

(54) DRUG DISCOVERY SCREENING APPARATUS

(75) Inventors: Taichirou Nedu, Musashino (JP);
Kouichi Yamamoto, Musashino (JP);
Takayuki Kei, Musashino (JP);
Toshiyuki Suzuki, Musashino (JP)

(73) Assignee: Yokogawa Electric Corporation, Musashino-shi, Tokyo (JP)

(*) Notice: Subject to any disclaimer, the term of this patent is extended or adjusted under 35 U.S.C. 154(b) by 115 days.

(21) Appl. No.: 12/704,865

(22) Filed: Feb. 12, 2010

(65) Prior Publication Data
US 2010/0211211 A1 Aug. 19, 2010

(30) Foreign Application Priority Data

Feb. 13, 2009 (JP) .................... 2009-030999
Mar. 4, 2009 (JP) .................... 2009-050065

(51) Int. Cl.
*G01N 35/02* (2006.01)
*G01N 35/04* (2006.01)

(52) U.S. Cl. ......... 422/65; 422/63; 422/67; 435/303.1; 435/287.2; 436/47; 436/48

(58) Field of Classification Search .............. None
See application file for complete search history.

(56) References Cited

U.S. PATENT DOCUMENTS

| 5,106,584 A * | 4/1992 | Funakubo et al. ............ 422/65 |
| 6,068,393 A * | 5/2000 | Hutchins et al. ............ 700/112 |
| 6,730,517 B1 * | 5/2004 | Koster et al. ................ 436/47 |
| 2002/0090320 A1 * | 7/2002 | Burow et al. ................ 422/64 |
| 2006/0216207 A1 * | 9/2006 | Lehto ....................... 422/100 |

FOREIGN PATENT DOCUMENTS

| JP | 61-074572 A | 4/1986 |
| JP | 11-079314 A | 3/1999 |
| JP | 11-287809 A | 10/1999 |
| JP | 2000-219305 A | 8/2000 |
| JP | 2002-202315 A | 7/2002 |

* cited by examiner

*Primary Examiner* — P. Kathryn Wright
(74) *Attorney, Agent, or Firm* — Westerman, Hattori, Daniels & Adrian, LLP (57) ABSTRACT

A drug discovery screening apparatus improves a testing operation efficiency. The drug discovery screening apparatus comprises an image measurement unit, an incubator unit integrally connected to the image measurement unit, a fixed stage disposed at the incubator unit, first conveyance for taking out one of plates stored in a carousel of the incubator unit and conveying the plate onto the fixed stage, second conveyance for taking out the plate conveyed onto the fixed stage and conveying the plate onto an XY stage disposed at the image measurement unit, and a control unit. The second conveyance comprises first and second conveyance arms, respectively supported horizontally by a conveyance unit support section, which convey the plates onto the fixed stage and XY stage so as to allow the respective plates to cross each other.

6 Claims, 8 Drawing Sheets

1: INCUBATOR
2: HOUSING
3: DOOR
4: PLATE TAKE-IN-AND-OUT PORT
5: SHUTTER
6: DISPENSING UNIT
9: PLATE

FIG. 7(C) (PRIOR ART)

DRUG DISCOVERY SCREENING APPARATUS

FIELD OF THE INVENTION

The present invention relates to a screening apparatus for use in a drug discovery screening apparatus in a biochemical field, more specifically, relates to an improvement of conveying means for conveying plates stored in an incubator unit to an image measurement unit of the drug discovery screening apparatus.

BACKGROUND OF THE INVENTION

In a drug discovery screening for searching materials, having a peculiar efficacy relative to a specific object, from a biochemical material, there is executed a systematic test for varying various conditions relative to a large number of analytes to be tested. For this reason, it is required to execute operations such as culturing, analyzing a huge number of samples with high precision and high efficiency, so that dedicated drug discovery screening apparatuses of various configurations have been conventionally employed.

As these drug discovery screening apparatuses, a plurality of dedicated apparatuses, for example, apparatuses combining a stocker for storing therein plates, which plates stores thereon liquid samples such as analytes, reagents, and so forth, a dispenser for dispensing the analytes, reagents on these plates, and an incubator for holding, culturing the plates, upon dispensing, in a predetermined environment, and so forth have been generally known.

Figure 7A:
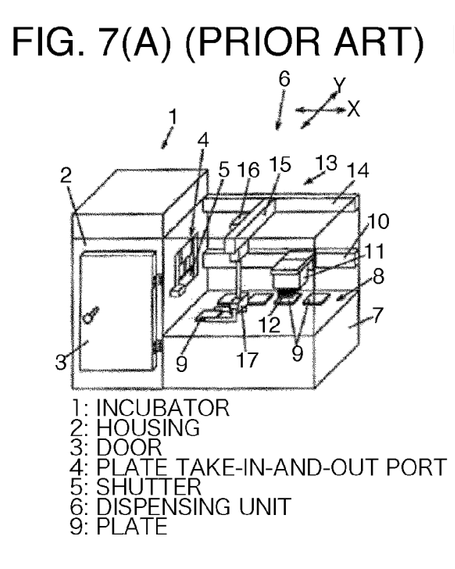
FIGS. 7(A) to 7(C) are views each showing a configuration of a prior art.
Figure 7B:
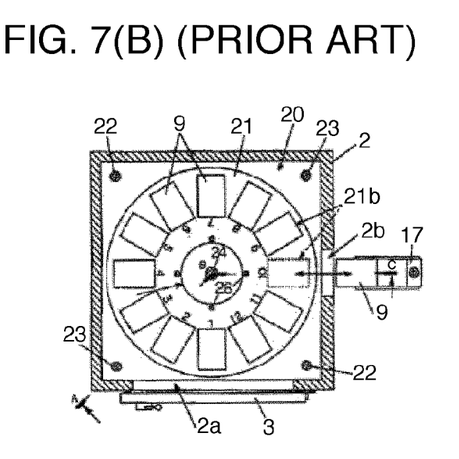
Figure 7C:
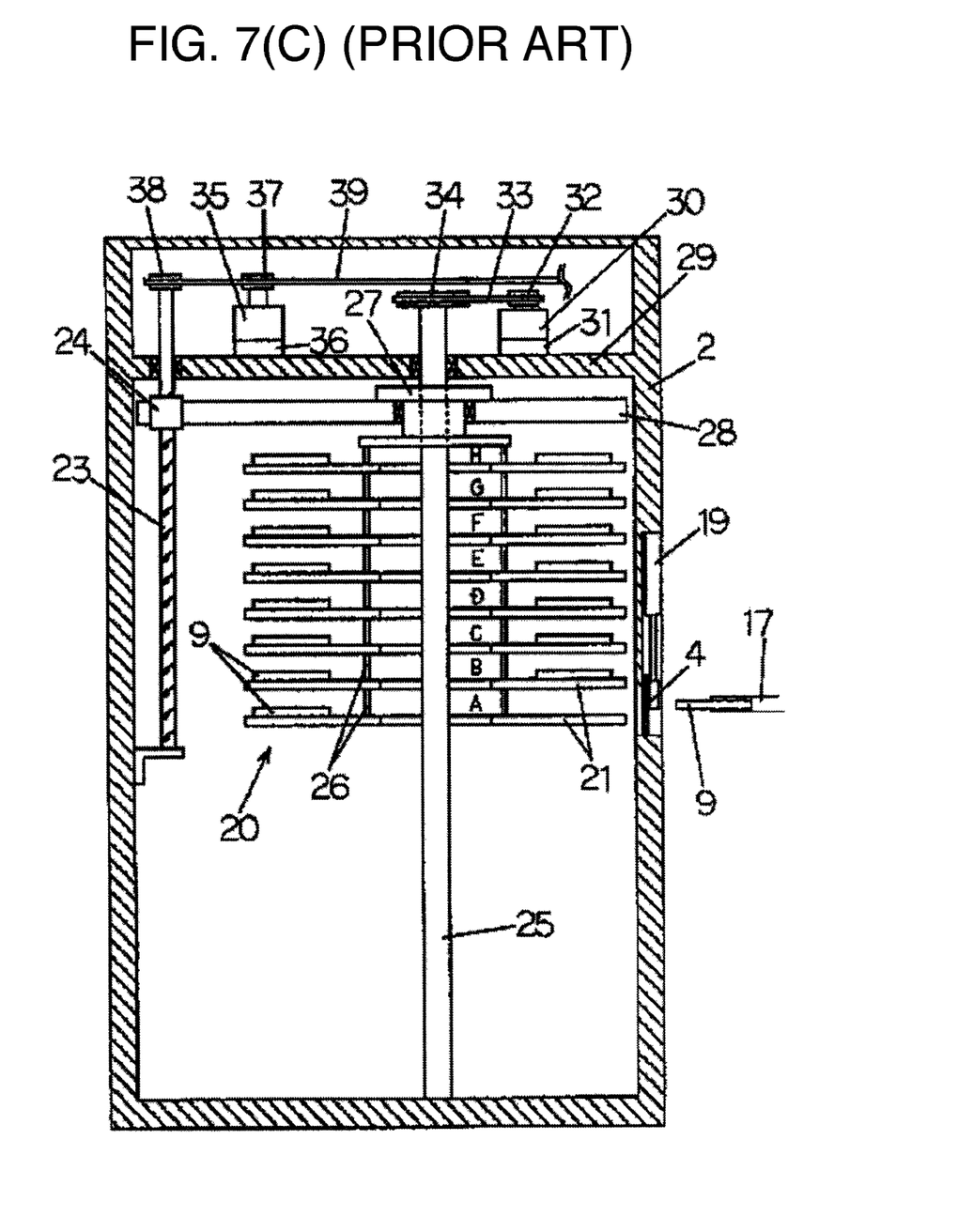

FIG. 7(A) is a perspective schematic view showing a conventional dispenser with an incubator, as disclosed in JP 2002-202315A, FIG. 7(B) is a plane sectional view of the apparatus in FIG. 7(A), and FIG. 7(C) is a side sectional view of the apparatus in FIG. 7(A).

In FIG. 7(A), an incubator 1 is provided with a door 3 at the front surface thereof, and a port 4 through which the plate 9 is taken in and taken out (hereinafter referred to as plate take-in-and-out port 4) at the side surface thereof.

The plate in-out port 4 is provided with a shutter 5. A dispenser 6 is disposed adjacent to the incubator 1. An upper surface of a base 7 of the dispenser 6 forms a dispensing stage 8, and a plurality of plates 9 are placed on the dispensing stage 8. Each plate 9 is a container provided with a large number of wells, and each well stores therein a sample including a biochemical material, and so forth. An X-axis table 10 is disposed on the dispensing stage 8, and a dispensing head 11, on which a large number of dispensing chips 12 are mounted, is connected to the dispensing stage 8.

The dispensing head 11 moves within the dispensing stage 8 by driving the X-axis table 10, and executes dispensing operation, namely, it intakes a sample from one of the plates 9, which are placed on the dispensing stage 8, and discharges the sample to another plate.

A plate conveyance mechanism 13 is provided on the dispensing stage 8. The plate conveyance mechanism 13 comprises an X-axis table 14, a Y-axis table 15, a Zθ-axis table 16 and a transfer table 17 connected to the Zθ-axis table 16. The plate conveyance mechanism 13 can execute, when it is driven, an operation for gripping the plate 9 on the dispensing stage 8 by the transfer table 17, conveying the plate 9 inside the incubator 1 or taking out the plate 9 from the incubator 1 through the plate take-in-out port 4.

In FIG. 7(B), a housing 2 has a heat insulating wall, and an environmental conditions inside the housing 2 such as a temperature, humidity, $CO_2$ concentration and so forth are kept to a predetermined condition by the environmental controller serving as an environment control unit (not shown).

A first opening part 2a is provided on the front surface of the housing 2 and is freely openable and closable by the door 3. A second opening part 2b is provided on the side surface of the housing 1, and is used as the plate take-in-out port 4. The second opening part 2b has a size capable of permitting the plate 9 to pass. The second opening part 2b is provided with the shutter 5, and the shutter 5 is vertically openable and closable and serves as a second door, and also it is automatically vertically movable.

Circular tables 21 are disposed inside the housing 2. A plurality of plates 9 are disposed on the circular tables 21. Numbers for specifying the positions are assigned clockwisely to placing parts 21b of the circular tables 21.

As shown in FIG. 7(C), a plurality of circular tables 21 are vertically connected to each other inside the housing 2 by connection members 26 to from a rotary rack 20. Symbols A, B, C, . . . are assigned to the respective circular tables 21 and respective circular tables 21 are specified by these symbols.

Numbers for specifying respective placing parts 21b of the rotary rack 20 are fixed by combining the symbols A, B, C, . . . of the respective circular table 21 and the numbers of the respective placing parts 21b of the circular tables 21. The rotary rack 20 executes a rotary motion around a spline shaft 25. A lifting plate 28 executes a lifting operation. The lifting plate 28 for executing the lifting operation is guided by two slide guides 22.

An R-axis motor 30, an Z-axis motor 35 are provide with encoders 31, 36, respectively, which issue pulse signals representing number of rotations of the R-axis motor 30 and Z-axis motor 35. Accordingly, if these pulse signal are counted, present positions of the placing parts 21b, to which the number of rack is assigned, can be specified, and the plates 9 placed on the placing parts 21b of the rack having arbitrary numbers can be positioned at the plate take-in-and-out port 4.

Patent Documents

Patent document JP 2002-202315A

Patent document JP 1999-287809A

However, the conventional drug discovery screening apparatus connects dedicated apparatuses such as the foregoing stocker and dispenser by use of conveyance means such as a robot, and so forth, thereby executing delivery of the plates between respective apparatuses. Accordingly, there arise problems in that a large space is needed for the entire drug discovery screening apparatus, thereby increasing facility costs, and a testing operation efficiency is low because the delivery of the plates between individual apparatuses, which are spaced from each other, has to be executed multiple times.

SUMMARY OF THE INVENTION

Accordingly, it is an object of the invention to provide a drug discovery screening apparatus capable of designing space saving, reducing facility costs, and improving testing operation efficiency.

To achieve the above object, according to the first item of the invention, the drug discovery screening apparatus comprises an image measurement unit, an incubator unit integrally connected to the image measurement unit, a fixed stage disposed at the incubator unit, first conveyance means for taking out one of plates stored in a carousel of the incubator unit and conveying the plate onto the fixed stage, second conveyance means for taking out the plate conveyed onto the fixed stage and conveying the plate onto an XY stage disposed at the image measurement unit, and a control unit for controlling operations of the image measurement unit and incubator unit, wherein the second conveyance means comprises a first conveyance arm and a second conveyance arm, respectively supported horizontally by a conveyance unit support section, and the first and second conveyance arms convey the plate onto the fixed stage and the plate on the XY stage so as to allow the respective plates to cross each other.

According to a second item of the invention, the first and second conveyance arms are vertically movable along the conveyance unit support section and provided with hands, each having predetermined length relative to the first and second conveyance arms for gripping the plates, and movable horizontally along, the first and second conveyance arms.

According to a third item of the invention, the incubator unit is provided with a plate transfer unit for placing thereon a plurality of plates in layers, and third conveyance means for taking the plate placed on the plate transfer unit in the carousel in response to an instruction from the control unit.

According to a fourth item of the invention, the image measurement unit is provided with stimulant infusion means having an infusion stage for infusing stimulant into at least one of a plurality of samples placed on the plate, and fourth conveyance means for taking out the plated conveyed onto the fixed stage and conveying the plate onto the infusion stage and also conveying the plate into which the stimulant is infused onto the XY stage.

According to a fifth item of the invention, the drug discovery screening apparatus is further provided with a teaching function for storing stopping positions of the plates, the plates being transferred to and placed on the fixed stage, infusion stage and XY stage, According to the invention, there are following advantages.

According to the first and second items of the invention, since the image measurement unit and incubator unit are integrally connected to each other, and first and second arms are horizontally supported by a conveyance unit support section disposed inside the incubator section, the first and second arms are vertically movable along the transfer unit support section and provided with hands each having a predetermined length relative to the first and second arms for gripping plates, and movable horizontally along the conveyance arms, wherein the first and second conveyance arms convey the plate onto the fixed stage and the plate onto the XY stage so as to allow the respective plates to cross each other, times for conveying the measured samples and the samples to be measured next can be reduced, thereby designing space saving, reducing facility costs, and improving a testing operation efficiency.

According to the third item of the invention, since the incubator unit is provided with the plate transfer unit for placing thereon a plurality of plates in layers, and third conveyance means for taking the plate placed on the plate transfer unit in the carousel in response to an instruction from the control unit, the testing operation can be executed without delay.

According to the fourth item of the invention, since the image measurement unit is provided with stimulant infusion means having an infusion stage for infusing stimulant into at least one of a plurality of samples placed on the plate, and fourth conveyance means for taking out the plated conveyed onto the fixed stage and conveying the plate onto the infusion stage and also conveying the plate into which the stimulant is infused onto the XY stage, a large number of samples can be automatically measured and the change of the sample at the time immediately after stimulant is infused in the sample can be observed.

According to the fifth item of the invention, since the drug discovery screening apparatus is further provided with a teaching function for storing stopping positions of the plates, the plates being transferred to and placed on the fixed stage, infusion stage and XY stage, minutes adjustment between the respective units in apparatus can be dispensed with, and the assembling and maintenance of apparatus can be simplified.

PREFERRED EMBODIMENT OF THE INVENTION

Figure 1:
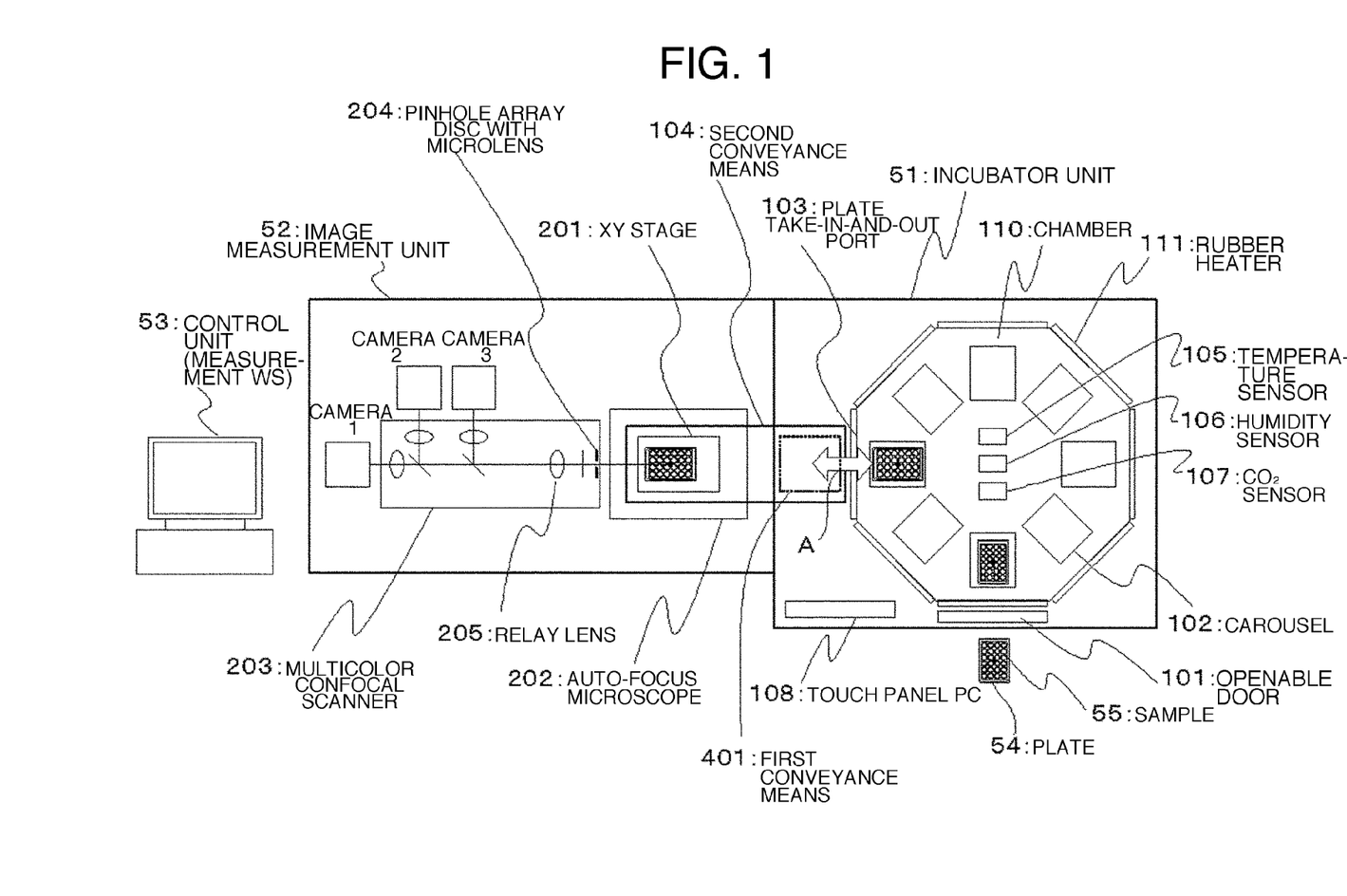
FIG. 1 is a view showing a configuration of an embodiment of the present invention.
Figure 2A:
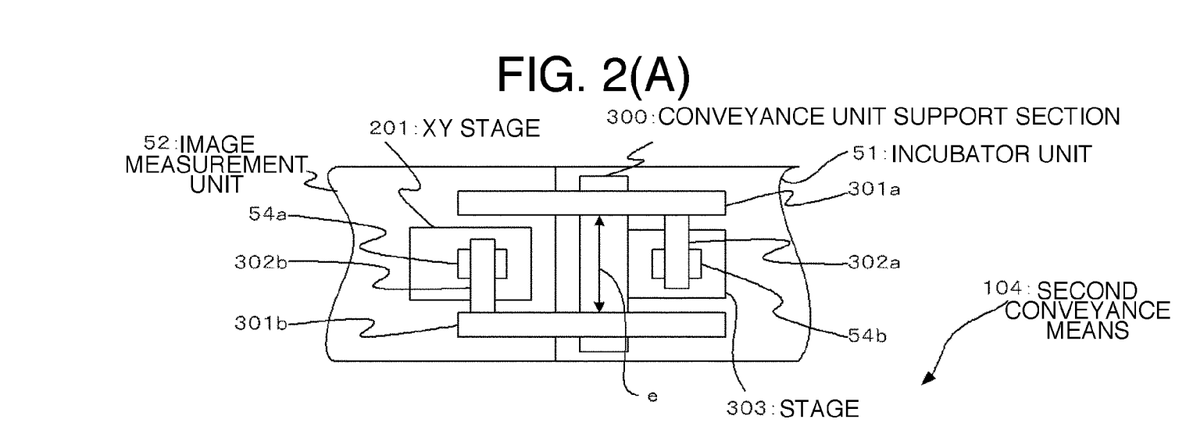
FIG. 2(A) is a plan view of second conveyance means and FIG. 2(B) is a side view of the second conveyance means.
Figure 2B:
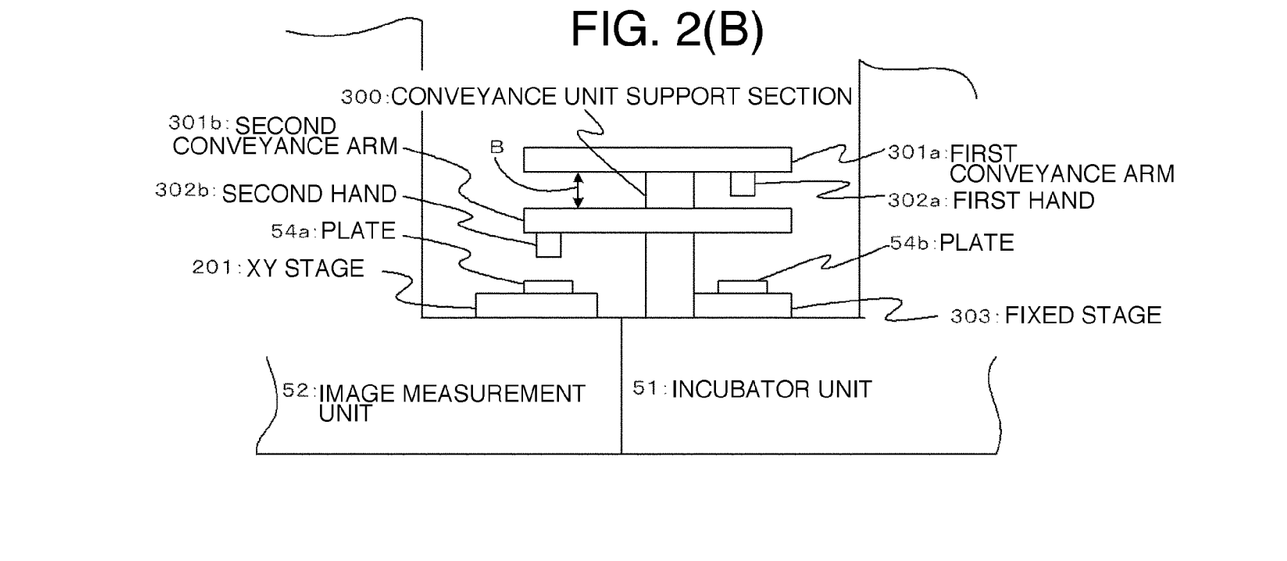

The present invention is now described in detail with reference to the attached drawings. FIG. 1 and FIG. 2 are views each showing a configuration of a first embodiment of the present invention.

In FIG. 1, an incubator unit 51 and an image measurement unit 52 are formed integrally with each other, and these units are controlled by a control unit 53. The incubator unit 51 is formed to have the same function as that of an incubator shown in FIG. 4.

A chamber 110 constituting the incubator unit 51 is formed in an octagonal cylindrical shape, and is heated by heating members (e.g. rubber heaters) 111 disposed at the upper, lower, and peripheral portions thereof. Live cells are monitored by a temperature sensor 105, a humidity sensor 106 and a $CO_2$ sensor 107, respectively disposed inside the chamber 110, and kept in an ideal predetermined atmosphere.

As for humidity, a water tank is installed inside the chamber 110, and the chamber 110 is kept at humidity of approximately 100%. As for $CO_2$ gas, high purity $CO_2$ is introduced in the chamber 110 from outside via a solenoid valve, and concentration of high purity $CO_2$ is measured by the $CO_2$ sensor, then the solenoid valve is opened and closed in response to the concentration of $CO_2$ gas thus measured.

The incubator unit 51 is provided with a touch panel PC 108, by which setting of the temperature, humidity and concentration of $CO_2$ gas is executed.

Depicted by 101 is an openable door 101 disposed at a front surface of the chamber 110, and depicted by 102 is a carousel disposed inside the chamber. By opening the door 101, a plate 54, on which plurality sample 55 are arranged, is introduced into the chamber 110 and placed on the carousel 102.

There are multiple carousels 102 and each carousel 102 is provided with a plurality of stages for storing therein plates 64.

The image measurement unit 52 stores therein an XY stage 201 for moving the sample placed on the plate, a microscope with auto-focus function (hereinafter referred to as auto-focus microscope 202) for enlarges and displays the sample, a multicolor confocal scanner 203 comprising a pinhole array disc 204 with microlens and a relay lens 205, and do forth, and a plurality of cameras.

FIG. 2(A) is a plan view of second conveyor means 104 and FIG. 2(B) is a side view of the second conveyor means 104. Meanwhile, only main constituents of the incubator unit 51 and image measurement unit 52 are illustrated in FIG. 2(A) and FIG. 2(B).

In FIG. 2(A) and FIG. 2(B), depicted by 300 is a conveyance unit support section, which is formed in a rectangular shape and fixed to the incubator unit 51. Depicted by 301a is a first conveyance arm and 301b is a second conveyance arm, and approximate central of these first and second conveyance arms are disposed close to both ends of the conveyance unit support section 300 with a predetermined space (e), as shown in FIG. 2(A).

Depicted by 302a and 302b are hands attached to the first and second conveyance arms 301a, 302b at respective one end thereof, respectively. The hands 302a and 302b are provided horizontally along the first and second conveyance arms 301a, 301b and attached perpendicularly to the first and second conveyance arms 301a and 301b so as to be in parallel with each other and face each other. Gripping means (not shown) for gripping the plates 54a and 54b are formed on respective other ends of the hands 302a and 302b.

The first and second conveyance arms 301a, 301b are attached to the conveyance unit support section 300 so as to be movable vertically relative to the conveyance unit support section 300 in a state where they are supported by the conveyance unit support section 300, while the first and second hands 302a and 302b are attached to the first and second conveyance arms 301a and 301b so as to be movable along the first and second conveyance arms 301a and 301b.

Meanwhile, as shown in FIG. 2(B), when the first and second hands 302a and 302b are moved, the movement of the first and second conveyance arms 301a and 301b is executed with a predetermined space (B) so that the first and second hands 302a and 302b do not collide with each other.

Depicted by 303 is a fixed stage, which is disposed in the vicinity of a plate take-in-and-out port 103 at the side of the incubator unit 51 and places thereon the plate, which is taken out via the plate take-in-and-out port 103. Depicted by 201 is an XY stage, which is disposed inside the image measurement unit 52, for moving each sample stored in each plate to a predetermined spot.

In FIG. 1, the plate 54 is conveyed to the plate take-in-and-out port 103, which is formed on the side surface of the chamber 110, by the rotation of the carousel 102, and it is placed on the fixed stage 303 by first conveyance means 401 (shown by dotted lines), which is driven in the direction of the arrow A.

In FIGS. 2(A) and 2(B), the plate 54b placed on the fixed stage 303 is gripped, for example, by the first hand 302a to be lifted up to a predetermined height. During that period, namely, when the plate 54b is lifted up to a predetermined height, the plate 54a, which was placed on the XY stage 201, upon completion of measurement thereof, was gripped by the second hand 302b and is lifted up to a predetermined height (where both hands do not collide with each other when they cross each other), which is different from the height of the first hand 302a.

Both hands 302a, 302b move horizontally along their respective arms 301a, 301b, so that the plate 54a, upon completion of measurement thereof, is placed on the fixed stage 303, and the plate 54b to be measured is placed on the XY stage 201.

During the measurement of plate 54b to be measured on the XY stage 201, the plate 54a on the fixed sage 303 is conveyed to a predetermined carousel within the chamber 110 by the first conveyance means 401 (shown by dotted lines), which is driven in the direction of the arrow A, thereafter a fresh plate is placed on the fixed stage 303.

There is an advantage in enhancing a throughput of conveyance by the provision of two arms and two hands as set forth above. That is, when a plurality of sample plates are to be sequentially measured, for example, the first arm and first hand grip the plate to be measured next while the second arm and second hand grip the plate, measurement of which was completed, thereafter both hands lift up both plates, subsequently both hands are moved horizontally while crossing each other, thereby exchanging one plate for another. With such a series of operations, the throughput of the apparatus can be dramatically enhanced compared with the apparatus provided with only one arm.

Meanwhile, with the drug discovery screening apparatus described above, operations of taking out the plate from the incubator unit 51, transferring it to the image measurement unit 52, where the sample was subjected to measurement, then returning the plate to the incubator unit 51 are repeatedly executed so as to execute tracking, analysis and so forth of the sample (cell) on the plate for a long period of time.

Accordingly, it is necessary to ensure specific positioning accuracy of two hands when the samples (cells) are conveyed so as to execute the tracking of the cells with reliability. Securement of the positioning accuracy can be implemented by adjusting the position of the XY stage 201 disposed at the image measurement unit 52, the position of the fixed stage 303 disposed at the incubator unit 51, and also the stopping positions of two hands at the time when two hands set the plates to the XY stage 201 and the fixed stage 303.

According to the invention, there is employed a system of teaching the position of the XY stage 201 to align with the stopping positions of the first and second hands. More specifically, the stopping positions of the hands each having a movable mechanism are adjusted with reference to the fixed stage 303 having no movable mechanism, thereby aligning two hand with the position of the fixed stage 303.

Next, the system stores a stopping position where the XY stage 201 receives the plate aligning with a position when the first and second hands convey the plate, and release the plate onto the XY stage 201, and determines the stopping position.

The drug discovery screening apparatus provided with such a teaching function can dramatically reduce the time of assembling the components without mechanically and minutely adjusting the positions of the stage and hands. At the time of occurrence of time-dependent change of the apparatus or maintenance of the apparatus, the teaching of the XY stage may be executed again (since the plate 54 needs not be moved in the XY direction in the incubator unit 51, the fixed stage 303 has normally no movable mechanism in the XY direction).

Figure 3:
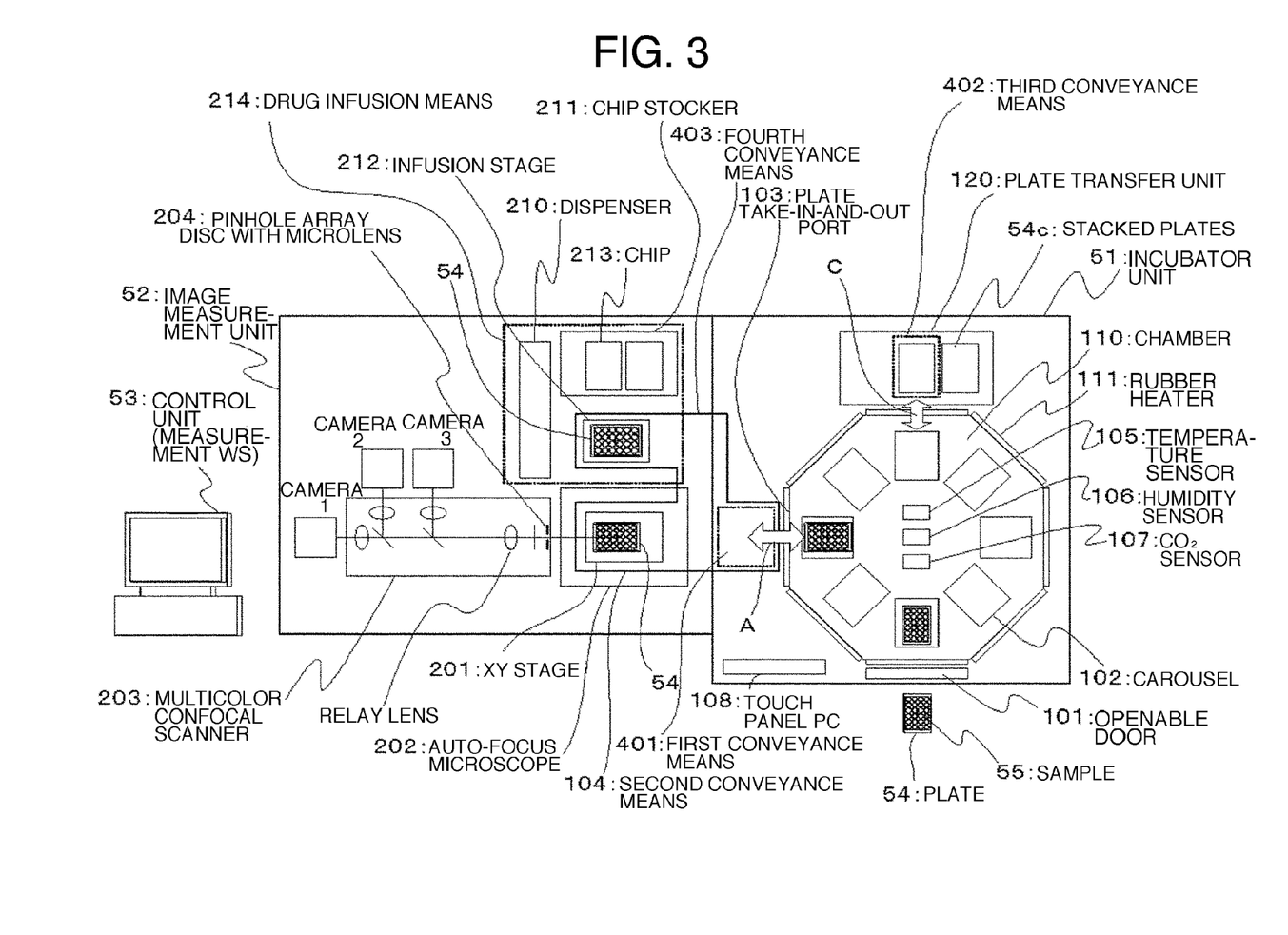
FIG. 3 is a view showing a configuration of another embodiment of the present invention.

FIG. 3 is a view for explaining a configuration of a drug discovery screening apparatus according to another embodiment comprising a plate transfer unit 120, third conveyance means 402 and drug infusion means including a fourth conveyance means 403, which are added to the configuration of the drug discovery screening apparatus of the first embodiment shown in FIG. 1, wherein a plurality of plates placed on the plate transfer unit 120 are taken in or out by the third and fourth conveyance means 402 and 403 between an incubator unit 51 and an image measurement unit 52.

In the second embodiment, the plate transfer unit 120 is provided at the back surface side (the side opposite to an openable door 101) of the incubator unit 51.

The plate is taken in or out in the direction of an arrow C by the third conveyance means 402 (shown by dotted lines) via a plate take-in-and-out port (illustration is omitted). It is decided in response to an instruction from a control unit 53 as to which carousel 102 at what timing the plate is taken in or out from.

The drug infusion means 214 is provided in the image measurement unit 52. A dispenser 210 constituting the drug infusion means 214 is a disposable type and a chip 213 is replenished by a chip stocker 211. More specifically, an operator sets stacked chips 213 to the chip stocker 211 from the back surface of the image measurement unit 52.

The dispenser 210 is provided with a mechanism, which moves in XYZ direction (illustration is omitted), and the chip 213 is mounted on a tip of the dispenser 210 by the XYX mechanism. Next, a stimulant such as a compound is sucked by an infusion stage 212, and the compound is conveyed over the plate 54 on the XY stage 201 by the fourth conveyor means 403, then it is dropped on the plate 54. Thereafter, change of the cell on the plate 54 is captured as an image. The foregoing operations are repeated so as to execute image-capturing operation for all the samples on the plate.

When the plate transfer unit 120 is installed in the incubator unit 51, an operator sets multiple pieces of stacked plates 54c to the plate transfer unit 120 from the back surface of the apparatus. Thereafter, the plate transfer unit 120 takes out the plate one by one sequentially from the lower portion thereof in response to an instruction from the control unit and transfers it to the carousel 102 inside the chamber.

A cell sample plate or a compound plate may be set to the plate transfer unit 120. For example, the cell plate is conveyed onto the XY stage 201 while the compound plate is conveyed onto the infusion stage 212, wherein compound is dropped from the compound plate to the cell plate by use of the dispenser 210, thereby measuring image of the cellular change of each sample.

Addition of the plate transfer unit 120 and the drug infusion means has a merit in enabling a large amount of samples to be measured automatically and capable of observing the change of the cell immediately after the compound is dropped.

Figure 4:
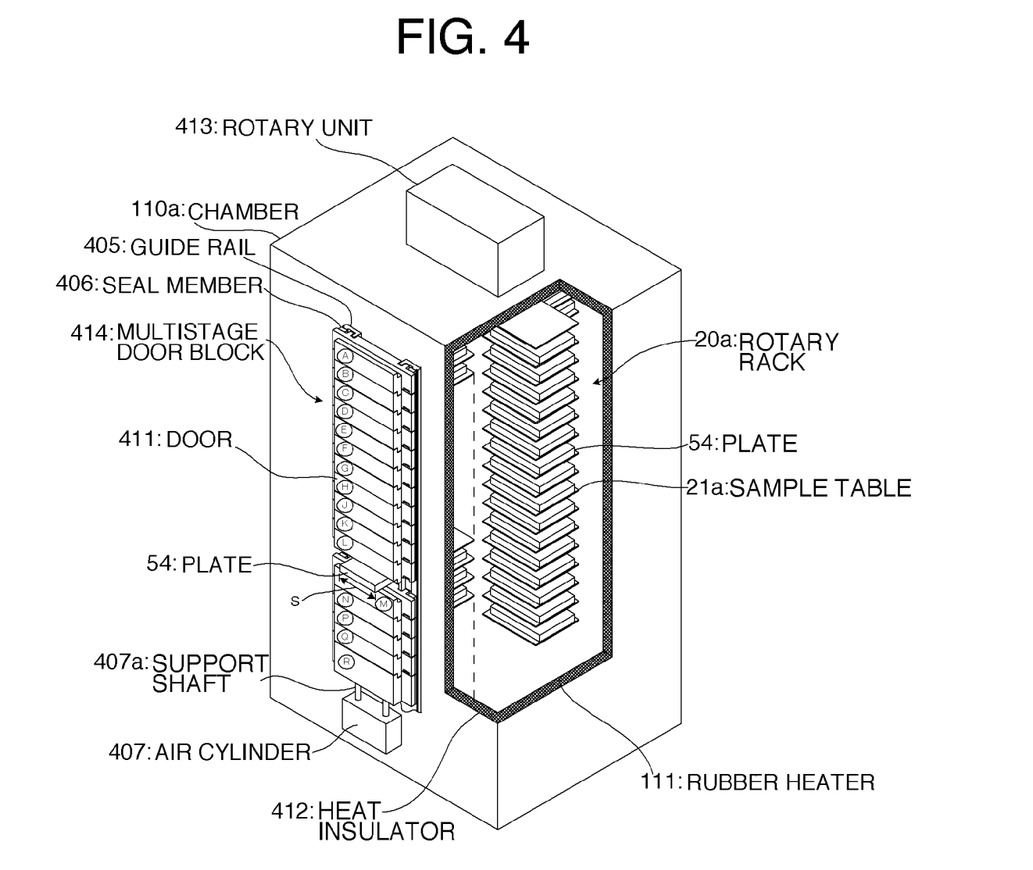
FIG. 4 is a perspective view showing a configuration of main constituents of a chamber constituting an incubator unit employed by the present invention.
Figure 5:
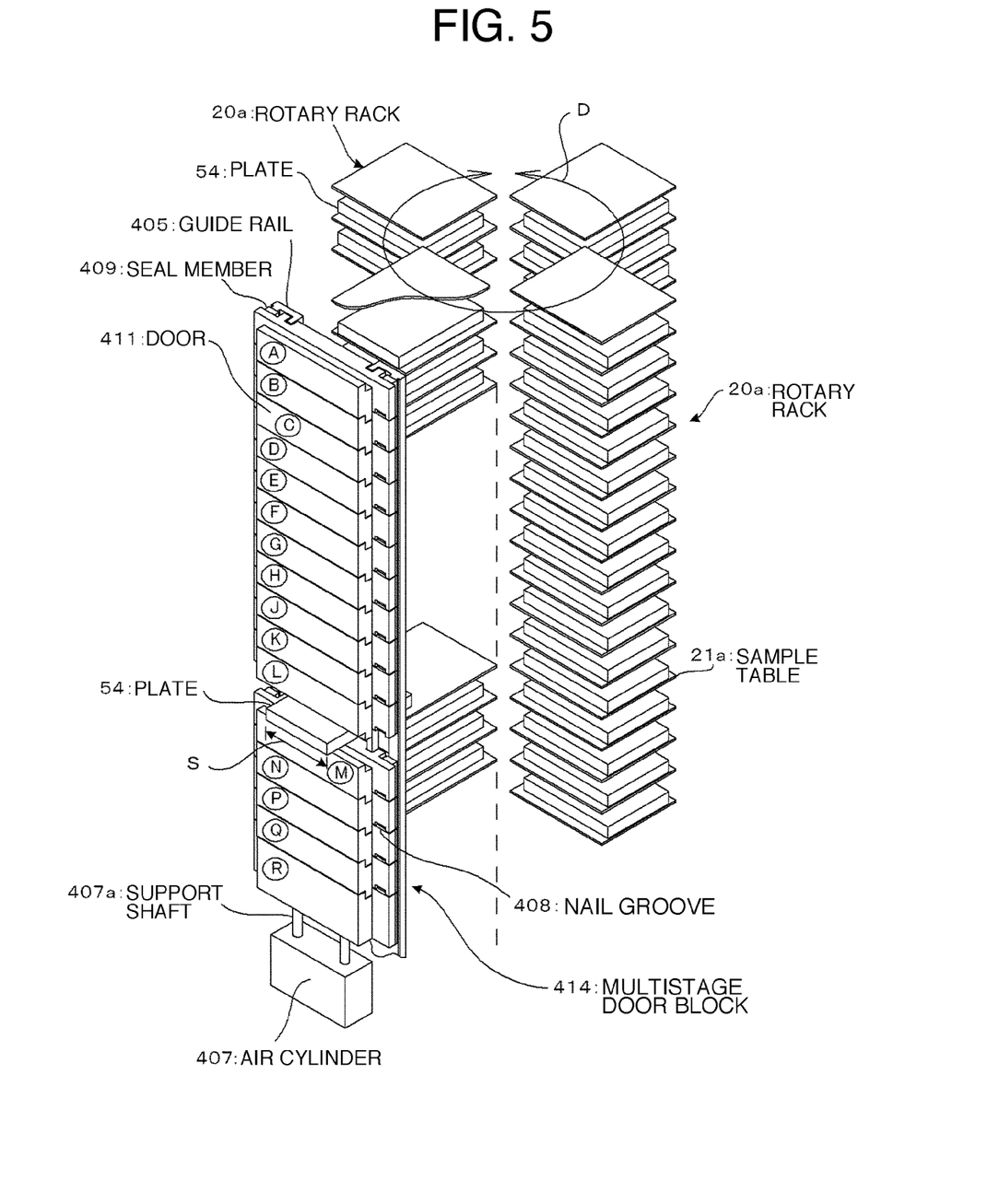
FIG. 5 is a perspective view showing a configuration of main constituents of the chamber shown in FIG. 4 removing a housing of the chamber.
Figure 6:
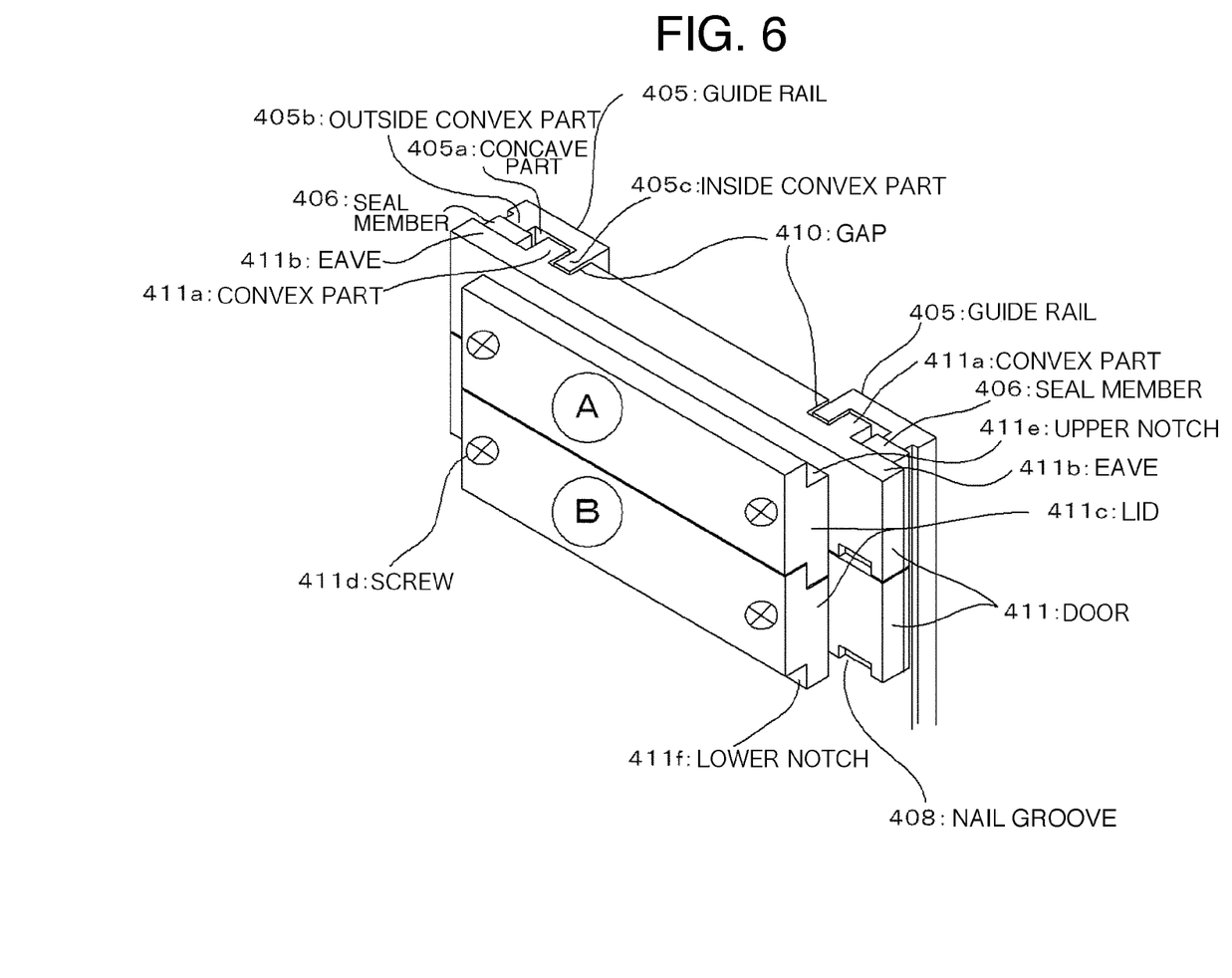
FIG. 6 is a view showing a detail of a plate take-in-out port.

FIG. 4, FIG. 5 and FIG. 6 are perspective views each showing an outline of a chamber and a configuration of a plate take-in-and-out port, respectively constituting the incubator unit. Although the chamber is represented by an octagonal shape in FIG. 1 and FIG. 3, it is represented by a rectangular shape in FIG. 4 and FIG. 5, which show a state where four rotary racks 20a are stored inside the chamber 110a.

The chamber 110a comprises a rubber heater 111 and a heat insulator 412, and a rotary unit 413 for rotating the rotary rack 20a in the direction of the arrow D (see FIG. 5) in response to an instruction from the control unit 53 is provided on the upper portion of the chamber 110a. It is assumed that an environment management for managing a temperature, humidity, concentration of $CO_2$ gas, and so forth is executed inside the chamber 110a.

In FIG. 4 and FIG. 5, the rotary rack 20a is configured by sample tables 21a disposed vertically with a predetermined interval and comprising multiple layers, and the plates 54 are placed on the sample tables 21a.

The rotary rack 20a is rotated by the rotary unit 413, and when one of the four rotary racks is positioned at the plate take-in-and-out port 103 (see FIG. 1), it is rendered in a state to face a multistage door block 414.

Guide rails 405 are disposed along both ends of a rectangular hole (not shown) formed on the side surface of the chamber 110a.

FIG. 6 is an enlarged view showing the detail of a part of a door 411 and guide rails.

In FIG. 6, the guide rails 405 are formed concave in a cross section, and outside convex portions 405b forming concave portions 405a are formed lower than inside convex portions 405c. Convex portions 411a are formed on the plurality of doors 411 in the vicinity of both ends thereof while facing the guide rails 405. As shown in FIG. 4 and FIG. 5, the doors 411 are disposed to have, for example, 16 pieces thereof (A to R).

The convex portions 411a of the doors 411 are inserted into the concave portions 405a, and in this insertion state, gaps 410 are generated. The chamber is configured such that although air inside the chamber invades in the gaps 410, but air that is subjected to environment management inside the chamber is not leaked outside the chamber by disposing the seal members 406 between eaves 411b formed at the right and left of the doors 411 and the outside convex portions 405b of the guide rails 405.

Lids 411c each have upper notches 411e at the upper side and lower notches 411f at the lower side, and the lids 411c are attached to the doors 411 via screws 411d, respectively. It is configured that the upper notches 411e and lower notches 411c are attached to the lids 411c, respectively, while there are rendered in an interlacing state, so that air inside the chamber is not leaked outside. Nail grooves 408 are formed at the portion close to both ends of the lower side of each door 411.

As shown in FIG. 4 and FIG. 5, an air cylinder 407 is disposed under the multistage door block 414 and it has two support shafts 407a, which stand upright in parallel with each other. Through holes (not shown) through which the support shafts 407a pass are formed on the doors 411 at the portions close to both ends thereof (located outside the horizontal width S of the plate 54). A plurality of doors 411 (A to R) are normally lifted up by powering on the air cylinder 407 to cover the rectangular hole formed on the side surface of the chamber 110a in whole, thereby preventing the plate 54 placed on the sample tables 21a from being taken in and out from the sample tables 21a through the rectangular hole.

With the foregoing configuration of the chamber 110a, if the plate corresponding to the door, e.g. M is taken in and out from the rectangular hole in response to the instruction from the control unit 53 (see FIG. 1), a nail of a robot (not shown) constituting the first conveyance means 401 (see FIG. 1) is inserted into the nail groove of the door L positioned above the door M by one stage.

If the air cylinder 407 is powered off in this state, the doors A to L are kept in the present state, but the doors M to R drop downward by one stage. As a result, the rectangular hole at the portion where the door M is located is exposed, so that the corresponding plate can be taken in or out from the sample table 21a through the rectangular hole. A robot (not shown) constituting the first conveyance means takes out the plate and conveys the plate onto the fixed stage 303 as shown in FIG. 2. After the plate is taken out, the air cylinder is powered on to lift up the doors M to R by one stage, thereby returning the doors M to R to the initial stage.

With the foregoing configuration of the chamber, only the door corresponding to the plate placed on a desired sample table is opened to execute plate take-in-out operation, so that a change in temperature, humidity and so forth inside the chamber can be kept to a minimum. Meanwhile, if the rotary rack 20a is rotated for every constant period, air inside the chamber is agitated to enable the environment of the plate 54 to keep constant.

The foregoing description merely represents specific and preferable embodiments aiming to explain and exemplify the present invention. According to the foregoing embodiments, the shape of the chamber is illustrated as octagonal and rectangular, it may be circular. Further, heating means for heating the chamber is not limited to the rubber heater, and it may be other heating means.

Further, it may be configured that air cylinders are embedded in the respective side surfaces of the doors A to R constituting the multistage door block 414 wherein the air cylinder located at specific door is actuated in response to the instruction of the control unit 43 (see FIG. 1), thereby opening and closing the specific door (the reliability of the opening and closing of the door is improved compared with a self-weight drop system shown in the embodiments.)

Still further, it may be configured that springs or air springs for supporting the weight of the doors A to R are provided at the lower side of the multistage door block 414, wherein the springs or air springs located at specific door are actuated in response to the instruction of a control unit 43, thereby vertically opening and closing the specific door.

Yet further, it is possible to improve a temperature distribution and prevent dew condensation by embedding heaters in the doors (A to R).

Yet still further, although the plate transfer unit is disposed at the back surface of the openable door but it may be disposed at the side surface thereof. Further, although the number of camera is limited to three according to the embodiments, but it may be any number if it is more than one. Accordingly, the present invention is not limited to the foregoing embodiments, and hence it may include many changes and variations unless deviating from the essence of the present invention.

What is claimed is:

1. A drug discovery screening apparatus, comprising:
an image measurement unit including an XY stage;
an incubator unit integrally connected to the image measurement unit, the incubator unit including a carousel and a fixed stage;
first conveyance means for conveying one of a plurality of plates between the carousel and the fixed stage;
second conveyance means for conveying at least one of the plurality of plates between the fixed stage and the XY stage, the second conveyance means comprising
a conveyance unit support section,
a first conveyance arm, and
a second conveyance arm, the first and second conveyance arms supported horizontally at different horizontal planes along the longitudinal axis of the conveyance unit support section, the first and second conveyance arms each being provided with hands for gripping the plates, the hands are movable horizontally along a respective one of the first and second conveyance arms; and
a control unit for controlling operations of the image measurement unit, second conveyance means, and incubator unit;
wherein the first and second conveyance arms can simultaneously convey one of the plurality of plates from the fixed stage to the XY stage and another of the plurality of plates from the XY stage to the fixed stage, such that two of the plurality of plates cross each other along the different horizontal planes,
wherein the first and second conveyance arms are vertically movable along the conveyance unit support section.

2. The drug discovery screening apparatus according to claim 1, wherein the control unit includes a memory that stores stopping positions of the plates on the fixed stage and the XY stage.

3. A drug discovery screening apparatus, comprising:
an image measurement unit including an XY stage;
an incubator unit integrally connected to the image measurement unit, the incubator unit including a carousel a fixed stage, a plate transfer unit for placing stacked plates thereon, and a third conveyance means for conveying plates sequentially one-by-one from the plate transfer unit to the carousel;
first conveyance means for conveying one of a plurality of plates between the carousel and the fixed stage;
second conveyance means for conveying at least one of the plurality of plates between the fixed stage and the XY stage, the second conveyance means comprising
a conveyance unit support section,
a first conveyance arm, and
a second conveyance arm, the first and second conveyance arms supported horizontally at different horizontal planes along the longitudinal axis of the conveyance unit support section, the first and second conveyance arms each being provided with hands for gripping the plates, the hands are movable horizontally along a respective one of the first and second conveyance arms; and
a control unit for controlling operations of the image measurement unit, second conveyance means, and incubator unit;
wherein the first and second conveyance arms can simultaneously convey one of the plurality of plates from the fixed stage to the XY stage and another of the plurality of plates from the XY stage to the fixed stage, such that two of the plurality of plates cross each other along the different horizontal planes, and
wherein the third conveyance means for conveying plates sequentially one-by-one transfers plates from the plate transfer unit to the carousel, in response to an instruction from the control unit.

4. The drug discovery screening apparatus according to claim 3, wherein the control unit includes a memory that stores stopping positions of the plates on the fixed stage and the XY stage.

5. A drug discovery screening apparatus, comprising:
an incubator unit integrally connected to the image measurement unit, the incubator unit including a carousel and a fixed stage;
an image measurement unit including an XY stage, a stimulant infusion means having an infusion stage for infusing stimulant into at least one of a plurality of samples placed on the plate, and a fourth conveyance means for conveying a plate between the fixed stage and the infusion stage, the fourth conveyance means also conveys a plate between the infusion stage and the XY stage;
first conveyance means for conveying one of a plurality of plates between the carousel and the fixed stage;
second conveyance means for conveying at least one of the plurality of plates between the fixed stage and the XY stage, the second conveyance means comprising
a conveyance unit support section,
a first conveyance arm, and
a second conveyance arm, the first and second conveyance arms supported horizontally at different horizontal planes along the longitudinal axis of the conveyance unit support section, the first and second conveyance arms each being provided with hands for gripping the plates, the hands are movable horizontally along a respective one of the first and second conveyance arms; and a control unit for controlling operations of the image measurement unit, second conveyance means, and incubator unit;

wherein the first and second conveyance arms can simultaneously convey one of the plurality of plates from the fixed stage to the XY stage and another of the plurality of plates from the XY stage to the fixed stage, such that two of the plurality of plates cross each other along the different horizontal planes.

6. The drug discovery screening apparatus according to claim 5, wherein the control unit includes a memory that stores stopping positions of the plates on the fixed stage, the infusion stage and the XY stage.

* * * * *